United States Patent
Takada et al.

(10) Patent No.: US 7,357,864 B2
(45) Date of Patent: Apr. 15, 2008

(54) MICROFLUIDIC DEVICE

(75) Inventors: Tetsuo Takada, Sakura (JP); Takanori Anazawa, Sakura (JP); Atsushi Teramae, Yachimata (JP)

(73) Assignee: Kawamura Institute of Chemical Research, Sakura-shi (JP)

( * ) Notice: Subject to any disclaimer, the term of this patent is extended or adjusted under 35 U.S.C. 154(b) by 323 days.

(21) Appl. No.: 10/548,169

(22) PCT Filed: Mar. 10, 2004

(86) PCT No.: PCT/JP2004/003096

§ 371 (c)(1),
(2), (4) Date: Sep. 7, 2005

(87) PCT Pub. No.: WO2004/081559

PCT Pub. Date: Sep. 23, 2004

(65) Prior Publication Data

US 2006/0091051 A1 May 4, 2006

(30) Foreign Application Priority Data

Mar. 11, 2003 (JP) .............................. 2003-064912

(51) Int. Cl.
*B01D 15/08* (2006.01)
(52) U.S. Cl. ................. 210/198.2; 210/502.1; 210/635; 210/656; 422/70; 422/100; 204/601
(58) Field of Classification Search ............... 210/635, 210/656, 198.2, 502.1; 422/70, 100, 102; 204/601
See application file for complete search history.

(56) References Cited

U.S. PATENT DOCUMENTS

| 6,375,871 | B1 * | 4/2002 | Bentsen et al. | 264/1.6 |
| 6,494,433 | B2 * | 12/2002 | Mastrangelo et al. | 251/11 |
| 6,761,962 | B2 * | 7/2004 | Bentsen et al. | 428/188 |
| 6,905,816 | B2 * | 6/2005 | Jacobs et al. | 435/5 |
| 2002/0098124 | A1 * | 7/2002 | Bentsen et al. | 422/100 |
| 2003/0232450 | A1 * | 12/2003 | Yoshida | 436/180 |

FOREIGN PATENT DOCUMENTS

| EP | 1 295 846 A1 | 3/2003 |
| JP | 6-169756 | 6/1994 |
| JP | 10-7835 | 1/1998 |

(Continued)

*Primary Examiner*—Ernest G. Therkorn
(74) *Attorney, Agent, or Firm*—Kratz Quintos & Hanson, LLP (57) ABSTRACT

The object of the present invention is to provide a production process of a microfluidic device in which a porous resin layer, which is capable of optimally fixing a large amount of enzyme, antigen or other protein or catalyst on the inner surface of a minute channel of a microfluidic device without obstructing said channel, is formed at a uniform thickness on the surface of said channel.

In the present invention, by preliminarily forming a porous resin layer having a large number of pores in its surface on a substrate, and forming an indentation having a porous resin layer on its bottom surface by using an activating energy beam-curable composition on said porous resin layer, followed by forming a channel by adhering a member serving as a cover to said indentation, a porous resin layer can easily be formed at a uniform thickness on the surface of said channel.

9 Claims, 1 Drawing Sheet

FOREIGN PATENT DOCUMENTS

| | | |
|---|---|---|
| JP | 2000-1565 | 1/2000 |
| JP | 2000-2705 | 1/2000 |
| JP | 2000-46797 | 2/2000 |
| JP | 2000-288301 | 10/2000 |
| JP | 2002-122597 | 4/2002 |
| JP | 2004-97209 | 4/2004 |
| WO | WO 95/01559 A2 | 1/1995 |
| WO | WO 01/98199 A1 | 12/2001 |
| WO | EP 1295846 * | 3/2003 |

* cited by examiner

FIG.1

MICROFLUIDIC DEVICE

REFERENCE TO RELATED APPLICATIONS

This application is a 371 of PCT/JP04/03096 filed Mar. 10, 2004.

TECHNICAL FIELD

The present invention relates to a microfluidic device having a porous resin layer employing a three-dimensional mesh structure on the inner surface of a channel, and a production process thereof.

BACKGROUND ART

Attempts have begun in recent years to use microfluidic devices to analyze the components of fluids containing trace amounts of DNA, biological substances and so forth in various fields including medical diagnostics and biochemical testing.

Microfluidic devices are also referred to as microfluid devices, microfabricated devices, lab-on-a-chip and micro total analytical systems (μ-TAS), and are capable of accelerating reactions and analyses, reducing the amounts of required reagents and reducing waste products by carrying out reactions and analyses in minute, capillary channels contained within the device.

In the case of using such microfluidic devices to react with a sample in a fluid by fixing an enzyme, catalyst or functional group and so forth on the inside surface of a channel, or in the case of detecting DNA and so forth in a sample by fixing a probe such as a DNA fragment of a specific sequence, it is important to fix larger amounts of enzyme, catalyst or DNA fragments or other probes in order to improve reaction rate and analysis sensitivity.

The inside of the channel is preferably made to be porous in order to increase the fixed amount of a functional group, (bio)chemical substance or biological substance as described above in a channel. A known example of a channel in which a porous body is formed inside is that in which the entire inside of the channel is a porous body, and is formed by a method in which a silicon or aluminum sheet is made to be porous by etching and heat treatment within a range to a fixed depth from the surface of the sheet, followed by adhering a cover onto said porous surface (see Japanese Unexamined Patent Application, First Publication No. H6-169756). However, since the entire inside of this channel is porous, and the fluid that flows through this channel flows through the pores of said porous body, a high pressure of several hundred Kpa is required for the fluid to flow at an adequate flow rate through the channel. Consequently, the microfluidic device body and connecting ports for introducing the fluid were required to be of a rugged structure capable of withstanding high pressure. In addition, since the fixation density of these inorganic materials is small in addition to the types of functional groups introduced onto the surface being limited, they still ended up being inadequate even if a porous body was employed. Moreover, since silicon and metal are optically opaque, thereby preventing pigments and fluorescent pigments fixed to the inside of the porous body from being observed from the outside, they did not contribute to improvement of the sensitivity of light absorption or fluorescent detection. Since these materials are optically opaque, there is a large amount of scattering of excitation light during fluorescence measurement, and since excitation light unable to be completely cut out with a filter ends up entering the receiving side, the baseline of measured fluorescent intensity becomes higher, thereby inviting a decrease in the S/N ratio and a decrease in reliability. Moreover, since silicon and metal have high thermal conductivity, it is difficult to provide a temperature gradient in a channel, thereby placing limitations on use as a microfluidic device.

On the other hand, since resins (organic polymers) have numerous types of functional groups that can be introduced onto their surface, and the fixation densities of those functional groups are high, they are preferable for use as constituent materials of the inner surface of the channels of microfluidic devices (see Japanese Unexamined Patent Application, First Publication No. 2000-2705). However, in processes involving the formation of a grooved channel like that known as a production process of a resin microfluidic device (see, for example, Japanese Unexamined Patent Application, First Publication No. 2000-46797), although a process is described in which a grooved channel having minute surface irregularities on the bottom is formed by forming minute surface irregularities on the surface of a base material by electron etching, coating an activating energy beam-curable compound thereon, radiating an energy beam onto those portions other than the channel to cure the activating energy beam-curable compound, and removing the uncured activating energy beam-curable compound of the non-irradiated portion, since this only involves the providing of surface irregularities for imparting hydrophilicity to the channel bottom of said microfluidic device, a three-dimensional mesh-like porous layer is not formed. Although it is not known whether or not more probe is fixed by this microfluidic device having an inner surface with surface irregularities than by a microfluidic device in which the inner surface is not treated, according to a confirmatory experiment conducted by the inventors of the present invention, the degree of the increase was small and was not considered to be adequate.

On the other hand, a method of increasing the fixed amount of an enzyme or catalyst on the surface of a sheet and so forth instead of the surface of a channel is disclosed in which a thin porous layer is formed on the surface of said sheet followed by fixing the enzyme or catalyst thereon (see Japanese Unexamined Patent Application, First Publication No. 2000-2705). However, a method in which such a porous layer is provided on one side of the inner surface of a minute channel of a microfluidic device has heretofore not been known.

In addition, a method of producing a hydrophilic porous membrane is disclosed in which a mixed solution of an energy beam-curable resin, linear polymer and solvent is coated onto a base material and irradiated with energy followed by contacting with a non-solvent of the linear polymer to cause phase separation (see Japanese Unexamined Patent Application, First Publication No. 10-007,835). However, with respect to this method as well, a method of providing such a resin at a uniform thickness on the inner surface of a minute channel of a microfluidic device has heretofore not been known.

The objects to be solved by the present invention consist of providing a microfluidic device, in which a porous resin layer having a three-dimensional mesh structure, which is capable of optimally fixing a large amount of enzyme, antigen or other protein or catalyst on the inner surface of a minute channel of a microfluidic device without obstructing the channel of the microfluidic device, is formed at a uniform thickness on the surface of said channel, a microfluidic device in which said porous resin layer is formed at an arbitrary location in the direction of flow of the channel, a microfluidic device in which said porous resin layer is formed on a portion of the cross-section of the channel, and a production process of said microfluidic device.

DISCLOSURE OF THE INVENTION

As a result of conducting extensive studies on ways of achieving the aforementioned objects, the inventors of the present invention found that the aforementioned objects can be achieved by preliminarily forming a porous resin layer having a three-dimensional mesh structure on the surface of a substrate, and forming an indentation having a porous resin layer having a three-dimensional mesh structure on its bottom surface in said porous resin layer by using an activating energy beam-curable composition, followed by forming a channel by adhering a member serving as a cover to said indentation, thereby leading to completion of the present invention.

Namely, the present invention provides a microfluidic device comprising a substrate, a porous resin layer having a three-dimensional mesh structure, a channel and a cover; wherein, said microfluidic device (I) has said porous resin layer in the upper portion of the substrate, (II) said porous resin layer is filled with a curable resin of an activating energy beam-curable resin composition (X) impregnated excluding the channel portion, and (III) the channel has wall surfaces consisting of a porous resin layer having a three-dimensional mesh structure that is not filled with activating energy beam-curable resin composition (X), a curable resin layer of the activating energy beam-curable resin composition (X) formed in the upper portion of the porous resin layer having a three-dimensional mesh structure filled with the curable resin of activating energy beam-curable resin composition (X), and a cover, and is formed into the form of a cavity.

In addition, the present invention provides a production process of a microfluidic device comprising: (1) a step in which a porous resin layer having a three-dimensional mesh structure having a large number of pores is formed on the surface of a substrate; (2) a step in which an activating energy beam-curable composition (X) containing an activating energy beam-polymerizeable compound (a) is coated onto said porous resin layer, an uncured coating of said composition (X) is formed, an activating energy beam is radiated on the uncured coating other than at the portion to serve as the channel to form a cured or semi-cured coating of the compound (X), the uncured compound (X) at the non-irradiated portion is removed, and an indentation is formed in which a porous resin layer having a three-dimensional mesh structure is exposed on the bottom surface; and (3) another member serving as a cover is adhered to the indentation of the member having the indentation so that the indentation serves as a channel in the shape of a cavity; wherein, more preferably, the step in which a porous resin layer having a three-dimensional mesh structure is formed on the surface of the substrate consists of coating onto the substrate an activating energy beam-curable membrane deposition liquid (J) that contains an activating energy beam-polymerizeable compound (b) and a poor solvent (R) that is compatible with said compound (b) but incompatible with a polymer formed from said compound (b), followed by radiating an activating energy beam onto said membrane deposition liquid (J) and forming a porous resin layer having a three-dimensional mesh structure on the surface of the substrate.

In the case of using a microfluidic device of the present invention as a liquid chromatography member, since high-speed analysis is possible even if the developer is allowed to flow at low pressure, it is not necessary to give high pressure resistance to separation columns or connections between feed lines containing developer, and since the entire μ-TAS device does not require a rugged structure due to the ease of incorporating into μ-TAS, the separation target can be preferably separated even for minute sample volumes. In addition, since the fixed amounts of (bio) chemical substances having functional groups or molecule-recognizing functions can be made to be extremely large as compared with the prior art, the allowable sample feed volume can be increased resulting in improved quantification and accuracy as well as improved sensitivity. Moreover, since the device has high productivity and can be produced inexpensively, it can also be used for disposable applications.

In addition, since a porous resin layer having a three-dimensional mesh structure is able to be only formed on the bottom surface of the channel, the surface of said porous resin layer can be observed optically through the channel, thereby allowing highly sensitive and highly quantitative measurements.

In addition, in the case of using a microfluidic device of the present invention as a member for affinity electrophoresis, analyses can be performed by using as an electrophoresis medium without using a sol or gel, thereby eliminating the need for a complex preparation procedure prior to use, reducing deterioration of performance during market distribution and enabling storage in a dry state to facilitate storage and market distribution. In addition, since the fixed amounts of (bio)chemical substances having functional groups and molecule-recognizing functions can be made to be extremely large as compared with the prior art, the allowable sample feed volume can be increased resulting in improved quantification and accuracy as well as improved sensitivity. Moreover, since a porous resin layer having a three-dimensional mesh structure can be formed only on the bottom surface of the channel, the surface of said porous resin layer can be optically observed throughout the channel, thereby enabling highly sensitive and highly quantitative measurements.

In the case of using a microfluidic device of the present invention as a microarray member for DNA analysis or immunodiagnosis and so forth, the fixed amount of probe can be made to be extremely large as compared with the prior art, thereby resulting in improved detection sensitivity, improved quantitativeness and faster analyses. In addition, since the porous resin layer having a three-dimensional mesh structure is formed as a spot inside the channel and a different probe can be fixed at each spot, multiple parameters can be analyzed with a single channel. Moreover, since the porous resin layer having a three-dimensional mesh structure is able to be formed only on the bottom surface of the channel, the surface of said porous resin layer can be optically observed throughout the channel, thereby enabling highly sensitive and highly quantitative measurements.

In the case of using a microfluidic device of the present invention as a reaction tank or reaction tube of a microreactor, since the fixed amounts of catalysts, enzymes and so forth can be increased, reaction speed and yield are improved. In addition, since the porous resin layer having a three-dimensional mesh structure can be formed at an arbitrary region inside the channel, and a different catalyst and so forth can be fixed at each region, multiple stages of reactions can be carried out with a single channel.

Since the use of a production process of the present invention eliminates the difficulty and restrictions of having to subsequently form a porous resin layer in a narrow channel, a microfluidic device having a porous resin layer having a three-dimensional mesh structure of uniform thickness on the surface of a channel can be easily produced without obstructing said channel on the inner surface of the minute channel of the microfluidic device. In addition, the thickness, pore shape and pore diameter of said porous resin layer can be easily adjusted to optimum values for the purpose of use. Moreover, a porous resin layer forming portion having a three-dimensional mesh structure of an arbitrary length, such as a spot-shaped porous resin layer portion, is easily provided in a portion of the channel in the direction of flow. In addition, there is no leakage of fluid inside the channel through a portion of the porous resin layer other than the porous resin layer on the bottom of the channel.

According to a production process of the present invention, since the pore diameter and thickness of a porous resin layer having a three-dimensional mesh structure formed on the inner surface of a minute channel can be easily adjusted to optimum values for the purpose of use, specific surface area can be increased, a large amount of substance can be fixed, and (bio)chemical analysis and detection can be carried out in a short period of time with high sensitivity and high accuracy using a minimum amount of reagents. In addition, since a porous resin layer having a three-dimensional mesh structure can be formed only on the bottom surface of the channel, the surface of said porous resin layer can be optically observed throughout the channel, thereby enabling highly sensitive measurements in the case of using for analysis. Moreover, a porous resin layer forming portion of an arbitrary length, such as a spot-shaped porous resin layer portion, is easily provided in a portion of the channel in the direction of flow.

In addition, by providing a step in which the surface of a porous resin layer having a three-dimensional mesh structure is surface treated or modified following a step in which said porous resin layer is formed, reactive functional groups can be introduced onto the surface of said porous resin layer, and various types of (bio)chemical substances and biological substances can be fixed to the surface of said porous resin layer by covalent bonding by reacting with these functional groups. Naturally, these substances can also be fixed by adsorption by ionic bonding or hydrophobic bonding. At this time, a plurality of porous resin layer spots can be formed as previously described, different types and concentrations of functional groups can be introduced at each of said plurality of porous spots, or different types of substances can easily be fixed.

Moreover, as a result of making the viscosity of composition (X) 30 to 3000 mPa·s at 25° C., composition (X) rapidly penetrates the porous resin layer having a three-dimensional mesh structure when composition (X) is coated onto said porous resin layer, thereby allowing a microfluidic device to be produced easily without leakage of fluid in the channel through a portion of the porous resin layer other than the porous resin layer on the bottom of the channel. In addition, as a result of making the viscosity within the aforementioned range, composition (X) is completely removed from the porous resin layer when uncured composition (X) of the non-irradiated portion is removed after radiating with the activating energy beam.

BEST MODE FOR CARRYING OUT THE INVENTION

A production process of a microfluidic device having a three-dimensional mesh structure, porous resin layer on the inner surface of a channel of the present invention is at least comprised of the following steps (1) to (3):

(1) a step in which a porous resin layer having a three-dimensional mesh structure having a large number of pores is formed on the surface of a substrate;

(2) a step in which an activating energy beam-curable composition (X) containing an activating energy beam-polymerizeable compound (a) is coated onto said porous resin layer, an uncured coating of said composition (X) is formed, an activating energy beam is radiated onto the uncured coating other than at the portion to serve as the channel to form a cured or semi-cured coating of the compound (X), the uncured compound (X) at the non-irradiated portion is removed, and an indentation is formed in which a porous resin layer having a three-dimensional mesh structure is exposed on the bottom surface; and (3) another member serving as a cover is adhered to the indentation of the member having the indentation so that the indentation serves as a channel in the shape of a cavity.

A method of forming a porous resin layer having a three-dimensional mesh structure having a large number of pores in step (1) may be an arbitrary method provided said porous resin layer can be formed, and any of the four methods indicated below, for example, can be used. A three-dimensional mesh structure referred to here refers to a structure in which pores (voids) and a resin that serves as their matrix are respectively connected in the directions of three dimensions, and said pores open onto the surface of a porous resin layer. Examples include a structure in which air bubble-like cavities are mutually connected (also referred to as a sponge-like structure), a structure in which voids between mutually adhered resin particles are connected to form pores (also referred to as an aggregated particle-like structure or sintered body-like structure), a structure that is intermediate to these two structures in which the pores and resin have a nearly equivalent structure, and their respective layers are mutually connected (also referred to a modulated structure or gyroid structure), and a non-woven fabric-like structure (also referred to as a matte-like structure).

A first method of forming a porous resin layer having a three-dimensional mesh structure consists of forming a porous resin layer having a three-dimensional mesh structure by coating an activating energy beam-curable membrane deposition liquid (J) (to be referred to as membrane deposition liquid (J)) containing an activating energy beam-polymerizeable compound (b) (to be referred to as polymerizeable compound (b)) and a poor solvent (R) that is compatible with the aforementioned compound (b) but incompatible with a polymer formed from compound (b) to polymerize the aforementioned compound (b) and cause phase separation (this method is to be referred to as the reaction induction-type phase separation method). In this method, as a result of polymerization of compound (b), poor solvent (R) becomes no longer compatible with the polymer that is formed, phase separation occurs between the polymer and poor solvent (R), and poor solvent (R) is incorporated inside and between the deposited polymer. By then removing this poor solvent (R), the regions occupied by poor solvent (R) become pores, thereby enabling the formation of a porous resin layer having a three-dimensional mesh structure.

Polymerizeable compound (b) is polymerized by an activating energy beam in the presence or absence of a polymerization initiator, and is preferably an addition polymerizeable compound or compound having polymerizeable carbon-carbon double bonds as activated energy beam-polymerizeable functional groups, with highly reactive (meth)acrylic compounds, vinyl ethers and maleimide compounds that are cured even in the absence of a photopolymerization initiator being particularly preferable. Moreover, polymerizeable compound (b) is more preferably a compound that forms a crosslinked compound when polymerized since it is capable of enhancing shape retention in the semi-cured state and increasing strength after curing. Consequently, it is even more preferably a compound that has two or more polymerizeable carbon-carbon double bonds in a single molecule (the having of two or more addition polymerizeable functional groups in a single molecule is hereinafter referred to as being "multifunctional").

Examples of compounds that can be used for such a polymerizeable compound (b) include (meth)acrylic monomers, maleimide-based monomers and polymerizeable oligomers having a (meth)acryloyl group or maleimide group in their molecular chain.

Examples of the aforementioned (meth)acrylic monomers include difunctional monomers such as diethylene glycol di(meth)acrylate, neopentyl glycol di(meth)acrylate, 1,6-hexanediol di(meth)acrylate, 2,2'-bis(4-(meth)acryloyloxy-polyethyleneoxyphenyl)propane, 2,2'-bis(4-(meth)acryloyloxypolypropyleneoxyphenyl)propane, hydroxydipivalic acid neopentyl glycol di(meth)acrylate, dicyclopentanyl diacrylate, bis(acryloxyethyl)hydroxyethylisocyanurate and N-methylenebisacrylamide; trifunctional monomers such as trimethylol propane tri(meth)acrylate, trimethylol ethane tri(meth)acrylate, tris(acryloxyethyl)isocyanurate and caprolactone-modified tris(acryloxyethyl)isocyanurate; tetrafunctional monomers such as pentaerythritol tetra(meth) acrylate; and hexafunctional monomers such as dipentaerythritol hexa(meth)acrylate.

Examples of maleimide-based monomers include difunctional monomers such as 4,4'-methylenebis(N-phenylmaleimide), 2,3-bis(2,4,5-trimethyl-3-thienyl)maleimide, 1,2-bismaleimide ethane, 1,6-bismaleimide hexane, triethylene glycol bismaleimide, N,N'-m-phenylenedimaleimide, m-tolylendimaleimide, N,N'-1,4-phenylenedimaleimide, N,N'-diphenylmethane dimaleimide, N,N'-diphenyl ether dimaleimide, N,N'-diphenylsulfone dimaleimide, 1,4-bis(maleimidoethyl)-1,4-diazoniabicyclo-[2,2,2]octane dichloride, and 4,4'-isopropylidene diphenyl=dicyanate·N,N'-(methylenedi-p-phenylene) dimaleimide; and maleimides having a maleimide group such as N-(9-acridinyl)maleimide and a polymerizeable functional group other than a maleimide group. These maleimide-based monomers can also be copolymerized with compounds having polymerizeable carbon-carbon double bonds such as vinyl monomers, vinyl ethers and acrylic monomers.

Examples of polymerizeable oligomers having a (meth)acryloyl group or maleimide group in their molecular chain include those having a weight average molecular weight of 500 to 50000, specific examples of which include (meth)acrylic acid esters of epoxy resin, (meth)acrylic acid esters of polyether resin, (meth)acrylic acid esters of polybutadiene resin, and polyurethane resins having a (meth)acryloyl group on the end of their molecule.

These examples of polymerizeable compound (b) can be used alone or as a mixture of two or more types. In addition, they may also be used by mixing with monofunctional monomers such as monofunctional (meth)acrylic monomers and monofunctional maleimide-based monomers for the purpose of adjusting viscosity, adjusting adhesion or stickiness in the semi-cured state, or imparting functions such as reactivity or hydrophilicity. For example, amphiphilic compound (c) to be described later may also be added.

Examples of monofunctional (meth) acrylic monomers include methyl methacrylate, alkyl (meth)acrylate, isobornyl (meth)acrylate, alkoxy polyethylene glycol (meth)acrylate, phenoxy dialkyl (meth)acrylate, phenoxy polyethylene glycol (meth)acrylate, alkylphenoxy polyethylene glycol (meth)acrylate, nonylphenoxy polypropylene glycol (meth) acrylate, hydroxyalkyl (meth)acrylate, glycerol acrylate methacrylate, butanediol mono(meth)acrylate, 2-hydroxy-3-phenoxypropyl acrylate, 2-acryloyloxyethyl-2-hydroxypropylacrylate, ethylene oxide-modified phthalic acid acrylate, ω-carboxycaprolactone monoacrylate, 2-acryloyloxy propylhydrodiene phthalate, 2-acryloyloxy ethyl succinate, acrylic acid dimer, 2-acryloyloxy propylhexahydrohydrodiene phthalate, fluorine-substituted alkyl(meth)acrylate, chlorine-substituted alkyl(meth)acrylate, sodium sulfonate ethoxy (meth)acrylate, sulfonic acid-2-methylpropane-2-acrylamide, phosphoric acid ester group-containing (meth)acrylate, glycidyl(meth)acrylate, 2-isocyanato ethyl(meth)acrylate, (meth)acryloyl chloride, (meth)acrylaldehyde, sulfonic acid ester group-containing (meth)acrylate, silano group-containing (meth)acrylate, ((di)alkyl)amino group-containing (meth)acrylate, quaternary ((di)alkyl)ammonium group-containing (meth)acrylate, (N-alkyl)acrylamide, (N,N-dialkyl)acrylamide and acroloyl morpholine.

Examples of monofunctional maleimide-based monomers include N-alkyl maleimides such as N-methyl maleimide, N-ethyl maleimide, N-butyl maleimide and N-dodecyl maleimide; N-alicyclic maleimides such as N-cyclohexyl maleimide; N-benzyl maleimide; N-(substituted or non-substituted phenyl) maleimides such as N-phenyl maleimide, N-(alkylphenyl) maleimide, N-dialkoxyphenyl maleimide, N-(2-chlorophenyl) maleimide and 2,3-dichloro-N-(2,6-diethylphenyl) maleimide and 2,3-dichloro-N-(2-ethyl-6-methylphenyl) maleimide; maleimides having a halogen such as N-benzyl-2,3-dichloromaleimide and N-(4'-fluorophenyl)-2,3-dichloromaleimide; maleimides having a hydroxyl group such as hydroxyphenyl maleimide; maleimides having a carboxy group such as N-(4-carboxy-3-hydroxyphenyl) maleimide; maleimides having an alkoxy group such as N-methoxyphenyl maleimide; maleimides having an amino group such as N-[3-(diethylamino)propyl]maleimide; maleimides having a multicyclic aromatic group such as N-(1-pyrenyl) maleimide; and maleimides having a polycyclic aromatic compound such as N-(dimethylamino-4-methyl-3-coumarinyl) maleimide and N-(4-anilino-1-naphthyl) maleimide.

Monomers having functional groups and ionic functional groups capable of serving as anchors for fixing bio(chemical substances and biological substances, and for example, functional groups listed as examples of functional groups that can be preferably inserted into a porous resin layer having a three-dimensional mesh structure to be described later, are preferably used for these monofunctional monomers.

A poor solvent that is compatible with polymerizeable compound (b) but not compatible (not mutually soluble)

with a polymer produced from polymerizeable compound (b) is used for poor solvent (R) used in the reaction induction-type phase separation method. The degree of compatibility between poor solvent (R) and polymerizeable compound (b) should be such that allows the obtaining of a homogeneous membrane deposition liquid (J). Poor solvent (R) may be a single solvent or a mixed solvent, and in the case of a mixed solvent, its composite components alone may be that which is not compatible with polymerizeable compound (b) or that which dissolves a polymer of polymerizeable compound (b). Examples of poor solvent (R) include alkyl esters of fatty acids such as methyl decanoate, methyl octanoate and diisobutyl adipate; ketones such as diisobutyl ketone; alcohols such as decanol; and, mixtures of alcohol and water such as a mixture of 2-propanol or ethanol and water.

In a reaction induction-type phase separation method, the pore diameter and strength of the resulting porous resin layer having a three-dimensional mesh structure vary according to the content of compound (b) contained in membrane deposition liquid (J). Although the strength of said porous resin layer is improved the greater the content of compound (b), pore diameter tends to become smaller. The content of compound (b) is preferably within the range of 15 to 50% by weight, and more preferably 25 to 40% by weight. If the content of compound (b) is less than 15% by weight, the strength of said porous resin layer decreases, while if the content of compound (b) exceeds 50% by weight, it becomes increasingly difficult to adjust the pore diameter of said porous resin layer.

Various additives such as a polymerization initiator, solvent, surfactant, polymerization inhibitor or polymerization retardant may be added to membrane deposition liquid (J) in order to adjust the polymerization rate, degree of polymerization or pore diameter distribution and so forth.

There are no particular limitations on the polymerization initiator provided it is active with respect to an activating energy beam and polymerizes polymerizeable compound (b), and radical polymerization initiators, anionic polymerization initiators or cationic polymerization initiators can be used, examples of which include acetophenones such as p-tert-butyltrichloroacetophenone, 2,2'-diethoxyacetophenone and 2-hydroxy-2-methyl-1-phenylpropan-1-one; ketones such as benzophenone, 4,4'-bisdimethylaminobenzophenone, 2-chlorothioxantone, 2-methylthioxantone, 2-ethylthioxantone and 2-isopropylthioxantone; benzoin ethers such as benzoin, benzoin methyl ether, benzoin isopropyl ether and benzoin isobutyl ether; benzyl ketals such as benzyl dimethyl ketal and hydroxycyclohexyl phenyl ketone; and, azides such as N-azidosulfonyl phenyl maleimide. In addition, polymerizeable photopolymerization initiators such as maleimide-based compounds can also be used.

Examples of polymerization retardants and polymerization inhibitors include α-methyl styrene, 2,4-diphenyl-4-methyl-1-pentene and other activating energy beam-polymerizeable compounds such as vinyl monomers having a low polymerization rate; and, hindered phenols such as tert-butylphenol.

In addition, there are no particular limitations on the solvent added, and examples include alcohols such as ethanol, ketones such as acetone, amide-based solvents such as N,N-dimethylformamide and chlorine-based solvents such as methylene chloride.

In addition, known, commonly used surfactants, hydrophobic compounds, thickeners, modifiers, colorants, fluorochromes, ultraviolet absorbers, enzymes, proteins, cells or catalysts and so forth can also be added to impart functions such as coatability and smoothness, or to adjust pattern resolution or the degree of hydrophilicity during lithographic pattern formation.

A substrate that can be used in a reaction induction-type phase separation method should be that which is substantially not attacked, for example not dissolved or decomposed, by membrane deposition liquid (J) or activating energy beam used.

Examples of such substrates include polymers; crystals such as glass or quartz; ceramics; semiconductors such as silicon; and metals, with polymers being particularly preferable. A polymer used for the substrate may be a homopolymer or copolymer, or a thermoplastic polymer or heat-curable polymer. In addition, the substrate may be composed of a polymer blend or polymer alloy, and may be a laminate or other composite material. Moreover, the substrate may also contain an additive such as a modifier, colorant, filler or reinforcing agent.

If a reaction induction-type phase separation method is used, a porous resin layer having a three-dimensional mesh structure can be formed in the manner of an aggregated particulate structure in which particulate polymers having a diameter of about 0.1 to 1 µm are mutually aggregated, or a sponge-like structure in which air bubbles having a diameter of 0.1 to 1 µm are mutually connected. In addition, in said reaction induction-type phase separation method, although a so-called isotropic membrane is normally formed in which the pore diameter of the pores is uniform in the direction of membrane thickness, a so-called heterogeneous membrane (also referred to as an asymmetrical membrane), in which pore diameter is distributed in the direction of membrane thickness, can also be formed by adding a volatile solvent to membrane deposition liquid (J), coating that liquid and then volatilizing and removing a portion thereof prior to irradiation with an activating energy beam. At this time, a layer having a small pore diameter (also referred to as a dense layer) can be formed on the surface in contact with the substrate on which is coated membrane deposition liquid (J) by adding a volatile good solvent, while a dense layer can be formed on the opposite side of the substrate by adding a volatile poor solvent or non-solvent. According to said reaction induction-type phase separation method, a porous resin layer having a three-dimensional mesh structure can be formed having a pore diameter of, for example, 0.05 to 5 µm.

In the present reaction induction-type phase separation method, in the case of forming a region or plurality of regions to which a porous resin layer having a three-dimensional mesh structure is limited, said porous resin layer can be formed on a portion of a substrate by, for example, (a) a method in which an activating energy beam-curable resin composition (X) is coated onto a portion of a substrate by a silk screen method and so forth followed by exposure, or (b) a method in which an activating energy beam-curable resin composition (X) is coated onto an entire substrate followed by pattern exposure. The present first method allows a functional group to be easily introduced into said porous resin layer by using a compound (b) having a functional group.

A second method of forming a porous resin layer having a three-dimensional mesh structure is a method in which, after contacting a substrate and a solvent (S) capable of dissolving or swelling said substrate, the solvent (S) is washed off using a solvent (T) that is compatible with solvent (S) but does not dissolve or swell said substrate to form said porous resin layer (said method is hereinafter to be referred to as the "surface swelling method"). In said method, a polymer that is dissolved or swollen by a solvent is used for the substrate, a solvent is contacted with the surface of said polymer, and after dissolving or swelling a portion of said substrate, by washing with a solvent that is not compatible with said polymer, said polymer aggregates in the form of a mesh resulting in the formation of a porous resin layer having a three-dimensional mesh structure.

Examples of a substrate used in the surface swelling method include styrene-based polymers such as polystyrene, poly-α-methylstyrene, polystyrene/maleic acid copolymer and polystyrene/acrylonitrile copolymer; polysulfone-based polymers such as polysulfone and polyether sulfone; (meth) acrylic polymers such as polymethyl methacrylate and polyacrylonitrile; polymaleimide-based polymers; polycarbonate-based polymers such as bisphenol A-based polycarbonate, bisphenol F-based polycarbonate and bisphenol Z-based polycarbonate; cellulose-based polymers such as cellulose acetate and methyl cellulose; polyurethane-based polymers; polyamide-based polymers; and, polyimide-based polymers.

There are no particular limitations on solvent (S) in the surface swelling method provided it is capable of dissolving or swelling the aforementioned substrate, examples of which include amide-based solvents such as N,N-dimethylformamide and N,N-dimethylacetoamide, dimethylsulfoxide and chloride-based solvents such as methylene chloride. In addition, these solvents can also be used in the form of mixed solvents by mixing.

Solvent (T) is a solvent that is miscible with solvent (S) and does not dissolve the substrate. Examples of solvent (T) include water, alcohols such as propanol, and mixtures of water and alcohol.

Examples of methods for contacting the substrate with solvent (S) include immersing the substrate in solvent (S), or spraying or spreading solvent (S) on the substrate surface.

Although examples of washing off solvent (S) with solvent (T) include a method in which solvent (S) is washed off by immersing in solvent (T), and a method in which solvent (S) is washed off by spraying with solvent (T), a method in which the entire substrate is immersed in solvent (T) is preferable.

A porous resin layer having a three-dimensional mesh structure produced by a surface swelling method is integrated with a substrate and is able to form a sponge-like or aggregated particle structure. The thickness of said porous resin layer can be controlled according to the duration of contact between the substrate and solvent (S), and the shorter the duration of contact, the less the thickness of said porous resin layer. It is necessary to suitably adjust the duration of contact between the substrate and solvent (S) according to the material and thickness of the substrate used, the type of solvent and so forth. If the duration of contact is too short, dissolution of the substrate does not proceed adequately and pores are not adequately formed. In addition, if the duration of contact is too long, the strength of the substrate decreases.

In the present surface swelling method, in the case of forming a porous resin layer having a three-dimensional mesh structure in a limited region or plurality of regions, a porous resin layer having a three-dimensional mesh structure can be formed on a portion of the substrate by using, for example, a method in which portions other than that where said porous resin layer is to be formed are covered with masking tape.

A third method of forming a porous resin layer having a three-dimensional mesh structure consists of forming a porous resin layer having a three-dimensional mesh structure on the surface of a substrate by coating a membrane deposition liquid (K), comprised by dissolving a linear polymer (P) in a solvent (U), and aggregating the linear polymer (P) in a porous form by contacting said substrate with a solvent (V) that does not dissolve or cause swelling of said linear polymer (P) and is compatible with solvent (U) (to be referred to as the wet method).

A linear polymer that forms a porous resin layer having a three-dimensional mesh structure by dissolving in solvent (U) can be used for a linear polymer (P) that can be used in the wet method. Linear polymers (P) such as styrene-based polymers, sulfone-based polymers, vinyl-based polymers, amide-based polymers, imide-based polymers, cellulose-based polymers, polycarbonates, acrylic polymers and so forth are preferable since they allow costs to be lowered and are handled easily.

A solvent similar to solvent (S) that can be used in the aforementioned surface swelling method can be used for solvent (U) in the wet method, while a solvent similar to solvent (T) in the aforementioned surface swelling method can be used for solvent (V).

In addition, various types of additives such as additives able to be used in the previously described reaction induction-type phase separation method may be added to membrane deposition liquid (K) as necessary.

Any arbitrary substrate may be used for the substrate used in the wet method, and although a substrate that is substantially attacked by membrane deposition liquid (K), in which linear polymer (P) is dissolved in solvent (U), is preferable, if a substrate is used that dissolves or swells in the aforementioned membrane deposition liquid (K), a porous resin layer having a three-dimensional mesh structure can be formed by a mechanism in which the aforementioned surface swelling method is added to the present wet method. Examples of such substrates include polymers; crystals such as glass and quartz; ceramics; semiconductors such as silicon; and metals. Polymers are particularly preferable.

The porous structure obtained according to the wet method may be a sponge-like structure, aggregated particle-like structure, gyroid structure or other complex shape having macrovoids.

In the case of using the wet method, although a heterogeneous membrane (asymmetrical membrane) having a dense layer is normally formed on the opposite side of a coated substrate, an isotropic membrane can also be formed by adding a salt or other low molecular weight compound (pore forming agent) or adjusting the boiling point of the poor solvent or good solvent and so forth. In addition, a porous resin layer having a three-dimensional mesh structure and pore diameter of 0.005 to 2 μm can be formed by adjusting the concentration of linear polymer (P), amount of solvent added and so forth.

In the present wet method, in the case of forming a porous resin layer having a three-dimensional mesh structure in a limited region or plurality of regions, a porous resin layer having a three-dimensional mesh structure can be formed on a portion of a substrate by, for example, a method in which membrane deposition liquid (K) is only coated at the portion where said porous resin layer is formed by screen printing and so forth, or a method in which those portions other than where said porous resin layer is formed are covered with masking tape.

A fourth method of forming a porous resin layer having a three-dimensional mesh structure consists of a method in which a porous resin layer having a three-dimensional mesh structure is formed by coating a membrane deposition liquid (L), in which an activating energy beam-polymerizeable compound (d), linear polymer (Q) and solvent (W) that dissolves them both are uniformly mixed, onto a substrate, polymerizing the polymerizeable compound (d) in solution by irradiating with an activating energy beam, and aggregating the linear polymer in a porous form by contacting said substrate with a solvent (N) that does not dissolve said linear polymer (Q) and is compatible with solvent (W) (to be referred to as energy beam-wet method).

In the present method, by using an activating energy beam-polymerizeable compound having a hydroxyl group, amino group, carboxyl group, aldehyde group, epoxy group or other arbitrary functional group for activating energy beam-polymerizeable compound (d) in the same manner as described in the section on activating energy beam-polymerizeable compound (b), these functional groups can be introduced onto the surface of a porous resin layer having a three-dimensional mesh structure more efficiently than the aforementioned reaction induction-type phase separation method.

Activating energy beam-polymerizeable compound (d) is preferably a crosslinking polymerizeable compound, and can be used by suitably selecting from the compounds listed as examples of the aforementioned activating energy beam-polymerizeable compound (b). Although the cured product of activating energy beam-polymerizeable compound (d) may be soluble or insoluble in solvent (W), in order to efficiently arrange the functional groups possessed by said compound (d) on the pore surface, said cured product is preferably soluble in solvent (W). Furthermore, when the cured product of said compound (d) is a crosslinked polymer, the term "soluble" should be read as "gelled", while the term "insoluble" should be read as "not gelled" (to apply similarly hereinafter).

In addition, although said compound (d) may be soluble or insoluble in solvent (N), a cured product of said compound (d) preferably gels when it is a crosslinked polymer in order to efficiently arrange functional groups possessed by said compound (d) on the pore surface, and is preferably insoluble in case the cured product of compound (d) is a non-crosslinked polymer to avoid running off.

Linear polymer (Q) is also arbitrary, and polymer listed as an example of the aforementioned linear polymer (P), for example, can be used. The use of a mixture of two or more types of linear polymer (Q) is preferable since the pore diameter of the surface of the porous resin layer having a three-dimensional mesh structure does not become excessively small, and it is difficult for macrovoids to form inside the porous resin layer having a three-dimensional mesh structure.

Although solvent (W) may or may not dissolve or swell a polymer formed from activating energy beam-polymerizeable compound (d), dissolving or swelling said polymer is preferable since functional groups can be fixed at high density on the pore surface. A solvent can be used for solvent (W) by suitably selecting from the solvents listed as examples of the aforementioned solvent (S).

Although solvent (N) preferable does not dissolve a polymer formed from activating energy beam-polymerizeable compound (d) in the case it is a non-crosslinked polymer, in the case said polymer is a crosslinked polymer, it may or may not swell said polymer. A solvent can be used for solvent (N) by suitably selecting from the solvents listed as examples of the aforementioned solvent (T).

In the present fourth method, in the case of forming a porous resin layer having a three-dimensional mesh structure in a limited region or plurality of regions, said porous resin layer can be formed on a portion of a substrate by, for example, a method in which membrane deposition liquid (L) is only coated at the portion where said porous resin layer is formed by screen printing and so forth, or a method in which those portions other than where said porous resin layer is formed are covered with masking tape.

The present fourth method allows functional groups to be easily introduced at high density on the pore surface of a porous resin layer having a three-dimensional mesh structure by using an activating energy beam-polymerizeable compound (d) having a functional group.

A porous resin layer having a three-dimensional mesh structure capable of being formed by the aforementioned examples of methods may be formed over the entire side of a substrate or on a portion of a substrate. In the case of the latter, a channel may be formed that passes through both a portion where said porous resin layer is formed and a portion where it is not formed. As a result, a microfluidic device can be formed that has a porous resin layer portion having a three-dimensional mesh structure at a portion of the bottom of the channel, but does not have said porous resin layer at other portions. At this time, by making the planar dimensions of the porous resin layer having a three-dimensional mesh structure formed on a portion of a substrate larger than the planar dimensions of the channel, it is not necessary to precisely align the locations of said porous resin layer and channel, thereby facilitating production. The porous resin layer having a three-dimensional mesh structure at a location other than the channel portion is filled with a cured product of activating energy beam-curable resin composition (X). For example, by forming said porous resin layer in n number of parallel lines (where n is a positive integer) on a substrate, and forming the channel oriented perpendicular to them, spots of a porous resin layer having a three-dimensional mesh structure can be formed at n locations within the channel without requiring precise alignment.

There are no particular limitations on the shape of the substrate used in the aforementioned examples of methods, and a substrate can be used that has an arbitrary shape according to the purpose of use. Although examples of such shapes include sheets (including films, ribbons and belts), plates, rolls and spheres, the coated surface is preferably planar or has a two-dimensional curvature from the viewpoint of facilitating coating of composition (X) thereon and facilitating irradiation with an activating energy beam.

The substrate may also be surface-treated in the case of a polymer or other material. Examples of the purposes of surface treatment include preventing dissolution by the membrane deposition liquid in the reaction induction-type phase separation method or wet method, improvement of wettability of the membrane deposition liquid, and improvement of adhesion of the porous resin layer having a three-dimensional mesh structure.

The method for surface treatment of the substrate is arbitrary, examples of which include treatment in which a composition containing a compound selected from the group of compounds listed as examples of polymerizeable compound (a) is coated onto the surface of the substrate and then cured by irradiating with an activating energy beam, corona treatment, plasma treatment, flame treatment, acid or base treatment, sulfonation treatment, fluorination treatment, primer treatment with a silane coupling agent and so forth, surface graft polymerization, coating with a surfactant or mold releasing agent, and physical treatment such as rubbing or sandblasting.

According to the aforementioned examples of methods, a porous resin layer having a sponge-like structure, aggregated particle-like structure, structure having macrovoids or structure consisting of a mixture of these shapes, can be formed on the surface of a substrate. In addition, since the resulting porous resin layer having a three-dimensional mesh structure has a large surface area in the form of the surfaces of a large number of pores, it is able to fix a large amount of catalyst, enzyme, DNA, sugar chains, cells or proteins.

If the surface of a porous resin layer having a three-dimensional mesh structure is made to be hydrophobic, enzymes, antigens and other proteins can be fixed to the surface of the porous resin layer having a three-dimensional mesh structure by hydrophobic interactions without having to introduce functional groups onto the porous surface. On the other hand, in the case of fixing proteins, DNA or sugar chains and so forth, by introducing a reactive functional group (such as an amino group, carboxyl group, hydroxyl group, epoxy group, aldehyde group, isocyanate group or —COCl group) onto the pore surfaces of the porous resin layer having a three-dimensional mesh structure in advance, and then reacting an amino group, hydroxyl group, phosphate group or carboxyl group of the aforementioned protein, DNA or sugar chain either directly or mediated by another functional group, the protein, DNA or sugar chain and so forth can be fixed to the surface of the porous resin layer having a three-dimensional mesh structure by covalent bonding.

The thickness of the porous resin layer having a three-dimensional mesh structure should be suitably selected according to the purpose of use. For example, in the case of using in affinity chromatography, the thickness of said porous resin layer is preferably 3 to 100 μm, and more preferably 5 to 50 μm.

The surface of the resulting porous resin layer having a three-dimensional mesh structure may be surface-treated using a method previously listed as an example of substrate surface treatment corresponding to the application. For example, the surface of said porous resin layer can be treated by a method such as coating a composition containing one or more types of compounds selected from the group of compounds listed as examples of polymerizeable compound (a) (and particularly hydrophilic and amphiphilic polymerizable compounds) onto the surface of said porous resin layer and curing by irradiating with an activating energy beam for the purpose of introducing a hydrophilic group, hydrophobic group and other functional groups onto the surface of said porous resin layer for the purpose of inhibiting non-specific absorption of a solute such as protein or DNA onto said porous resin layer surface.

In step (2), an uncured coating of composition (X) is formed inside a porous resin layer having a three-dimensional mesh structure and on said porous resin layer by coating composition (X) onto said porous resin layer to impregnate composition (X) inside said porous resin layer. Subsequently, an activating energy beam is radiated onto the uncured coating at those locations other than where a channel is to be formed to remove uncured composition (X) at the non-irradiated portions. As a result, an indentation is obtained in which the bottom surface is composed of said porous resin layer while the wall surface is composed of a cured or semi-cured coating of composition (X), and the pores of said porous resin layer at locations other than the portion serving as the channel are obstructed by a cured or semi-cured product of the impregnated composition (X).

Activating energy beam-polymerizeable compound (a) used in step (2) (to be referred to as polymerizeable compound (a)) is a compound that is able to be polymerized by an activating energy beam in the presence or absence of a polymerization initiator, and preferably is an addition polymerizeable compound or has polymerizeable carbon-carbon double bonds for the activating energy beam-polymerizeable functional groups. A highly reactive (meth)acrylic compound, vinyl ethers and maleimide-based compounds that are cured even in the absence of a photopolymerization initiator are particularly preferable.

In addition, if polymerizeable compound (a) is a multifunctional compound, strength after curing is also enhanced since a crosslinked structure is formed due to polymerization.

A compound similar to polymerizeable compound (b) able to be used in the aforementioned reaction induction-type phase separation method, for example, can be used for this polymerizeable compound (a).

Polymerizeable compound (a) can be used alone or as a mixture of two or more types. In addition, it may also be used after mixing with a monofunctional monomer in order to adjust viscosity or impart functions such as adhesiveness, stickiness or hydrophilicity.

A compound similar to the monofunctional monomers able to be used in the aforementioned reaction induction-type phase separation method, for example, can be used as a mixable monofunctional monomer.

Composition (X) contains at least the aforementioned polymerizeable compound (a). In addition to polymerizeable compound (a), said composition (X) preferably also contains amphiphilic polymerizable compound capable of copolymerizing with polymerizeable compound (a) (said amphiphilic polymerizable compound is to be referred to as amphiphilic compound (c)). As a result of composition (X) containing amphiphilic compound (c), the resulting cured product can be made to be resistant to swelling in water, and the surface of the cured product can be made to be hydrophilic and have low adsorbency with respect to biological components.

A compound that contains both hydrophilic groups and hydrophobic groups within its molecule, and has a polymerizeable compound capable of copolymerizing with activating energy beam-polymerizeable compound (a) contained in composition (X) by irradiating with an activating energy beam, can be used for amphiphilic compound (c). Although it is not necessary for amphiphilic compound (c) to become a crosslinked polymer, a compound that becomes a crosslinked polymer may be used. In addition, amphiphilic compound (c) should be that which is uniformly compatible with polymerizeable compound (a). Here, compatibility refers to not causing macroscopic phase separation, and includes a state in which micelles are formed and stably dispersed.

In the case polymerizeable compound (a) is a compound having two or more polymerizeable carbon-carbon unsaturated bonds in its molecule, amphiphilic compound (c) is preferably a compound having one or more polymerizeable carbon-carbon unsaturated bonds in its molecule.

Amphiphilic compound (c) is a compound that has a hydrophilic group and hydrophobic group in its molecule, and is compatible with water or hydrophobic solvent, respectively. In this case as well, compatibility refers to not causing macroscopic phase separation, and includes a state in which micelles are formed and stably dispersed.

Amphiphilic compound (c) preferably has solubility in water of 0.5% by weight or more at 0° C., and solubility in a mixed solvent of cyclohexane and toluene (5:1, weight ratio) at 25° of 25% by weight or more. Solubility referred to here indicates, for example, at least 0.5% by weight of the compound is able to be dissolved in the case of solubility of 0.5% by weight or more. If a compound is used for which at least solubility in water or solubility in cyclohexane and toluene (5:1, weight ratio) is lower than these values, it is difficult to obtain a cured product having superior characteristics for both surface hydrophilicity and hydrophobicity.

In the case amphiphilic compound (c) has a nonionic hydrophilic group, and particularly a polyether-based hydrophilic group, the balance between hydrophilicity and hydrophobicity in terms of Griffin's HLB value is preferably within the range of 11 to 16, and more preferably within the range of 11 to 15. If outside this range, it either becomes difficult to obtain a molded product having high hydrophilicity and superior moisture resistance, or the combination or mixing ratio of compounds for obtaining this ends up being limited.

The hydrophilic group possessed by amphiphilic compound (c) is arbitrary, and examples of which include cationic groups such as an amino group, quaternary ammonium group or phosphonium group; anionic groups such as a sulfone group, phosphoric acid group or carbonyl group; nonionic groups such as a hydroxyl group, polyethylene glycol chain or amide group; and amphoteric groups such as an amino acid residue. Amphiphilic compound (c) is preferably a compound having a polyether group as a hydrophilic group, and is particularly preferably a compound having 6 to 20 repeating polyethylene glycol chains.

Examples of hydrophobic groups of amphiphilic compound (c) include alkyl groups, alkylene groups, alkylphenyl groups, long-chain alkoxy groups, fluorine-substituted alkyl groups and siloxane groups. Amphiphilic compound (c) is preferably a compound having an alkyl group or alkylene group having 6 to 20 carbon atoms as a hydrophobic group. Alkyl or alkylene groups having 6 to 20 carbon atoms may be contained in the form of, for example, alkylphenyl groups, alkylphenoxy groups, alkoxy groups or phenylalkyl groups.

Amphiphilic compound (c) is preferably a compound having 6 to 20 repeating polyethylene glycol chains as a hydrophilic group, and an alkyl or alkylene group having 6 to 20 carbon atoms as a hydrophobic group. Among these amphiphilic compounds (c), nonylphenoxy polyethylene glycol (n=8-17) (meth)acrylate and nonylphenoxy polypropylene glycol (n=8-17) (meth)acrylate are particularly preferable.

Although differing according to the types and combination of polymerizeable compound (a) and amphiphilic compound (c), the preferable ratio of polymerizeable compound (a) and amphiphilic compound (c) contained in composition (X) is preferably 0.1 to 5 parts by weight, and more preferably 0.2 to 3 parts by weight, of amphiphilic compound (c) to 1 part by weight of polymerizeable compound (a). If the amount of amphiphilic compound (c) is less than 0.1 part by weight with respect to 1 part by weight of polymerizeable compound (a), it becomes difficult to form a highly hydrophilic surface, while if the amount of amphiphilic compound (c) exceeds 5 parts by weight, composition (X) swells in water and a polymer of composition (X) has the risk of gelling.

A cured product that demonstrates high hydrophilicity and low adsorptivity without gelling in a swollen state can be produced by suitably selecting the mixing ratio of polymerizeable compound (a) and amphiphilic compound (c). It is preferable to reduce the amount of amphiphilic compound (c) added the stronger the degree of hydrophilicity of amphiphilic compound (c), or for example, the larger Griffin's HLB value.

A polymerizeable compound (b) having a functional group to be introduced onto the surface of a porous resin layer having a three-dimensional mesh structure is preferably mixed into composition (X). In the case of introducing a certain functional group onto the surface of a porous resin layer having a three-dimensional mesh structure in particular, a resin having said functional group is preferably used for the resin that forms the porous resin layer having a three-dimensional mesh structure, and a polymerizeable compound (b) having said functional group is preferably mixed into composition (X). As a result, in a step to be described later in which uncured composition (X) at a non-irradiated portion is removed, even if the removal of composition (X) is incomplete, the problem of the pore surfaces being covered by precipitates of said composition thereby causing said functional group to not be exposed can be prevented.

In addition, a photopolymerization initiator, polymerization retardant, polymerization inhibitor, solvent, thickener, modifier or colorant and so forth can be mixed into composition (X).

Compounds similar to the photopolymerization initiators, polymerization retardants and polymerization inhibitors of membrane deposition liquid (J) in the aforementioned reaction induction-type phase separation method can be preferably used as photopolymerization initiators, polymerization retardants and polymerization inhibitors able to be added to composition (X).

Although there are no particular limitations on the solvent, it is necessary to suitably adjust the type and amount of solvent added according to additives added to the polymerizeable compound (a) and composition (X) used or according to the required viscosity and so forth. Examples of such solvents include alcohols such as ethanol, ketones such as acetone, amide-based solvents such as N,N-dimethylformamide, and chlorine-based solvents such as methylene chloride.

Although the viscosity of composition (X) can be changed according to the pore diameter of the porous resin layer having a three-dimensional mesh structure, the viscosity of composition (X) at 25° C. is preferably within the range of 30 to 3000 mPa·s, and more preferably within the range of 100 to 1000 mPa·s, from the viewpoint of allowing composition (X) to rapidly penetrate into the porous resin layer having a three-dimensional mesh structure when coating over the porous resin layer having a three-dimensional mesh structure, and composition (X) being completely removed from the porous resin layer having a three-dimensional mesh structure during removal of uncured composition (X) at a non-irradiated portion. If the viscosity of composition (X) is less than 30 mPa·s, it becomes difficult to control the depth of the indentation, and if the viscosity exceeds 3000 mPa·s, it becomes difficult for composition (X) to penetrate into the porous resin layer having a three-dimensional mesh structure, and removal of uncured composition (X) at a non-irradiated portion also becomes difficult.

In step (2), an arbitrary coating method can be used to coat composition (X) onto a porous resin layer having a three-dimensional mesh structure, examples of which include spin coating, roller coating, spreading, dipping, spraying, using a bar coater, using an X-Y applicator, screen printing, relief printing, gravure printing, extrusion from a nozzle and mold casting. In addition, in the case composition (X) has high viscosity or is particularly thinly coated, composition (X) can be coated by a method in which a solvent is contained in composition (X) and said solvent is volatilized after coating.

Although there are no particular limitations on the thickness at which composition (X) is coated provided that a cured or semi-cured coating is obtained on the upper portion of the surface of a porous resin layer having a three-dimensional mesh structure after irradiating with an activating energy beam, in the case of fixing a specific substance on said porous resin layer on a bottom surface and using for affinity chromatography, the thickness of a cured or semi-cured coating formed on the upper portion of said porous resin layer after irradiating with an activating energy beam, namely the wall height of an indentation, is preferably within the range of 3 to 150 µm, and more preferably within the range of 5 to 50 µm. If the thickness is less than 3 µm, there is the risk of the channel being obstructed when another member serving as a cover is adhered to the indentation to allow said indentation to serve as a cavity-like channel. On the other hand, if the thickness is greater than 150 µm, it becomes difficult for substances in an aqueous solution to be adsorbed to and released from (interact with) a porous resin layer having a three-dimensional mesh structure on the bottom surface of a channel while the aqueous solution passes through the channel, thereby making this unsuitable for affinity chromatography applications.

In the case of adding a solvent to activating energy beam-curable resin composition (X), said solvent is removed by volatilization following coating. The method of removal is arbitrary, and examples of methods that can be used include air drying, hot air drying, infrared light drying, vacuum drying and microwave drying. Although solvent may be removed after irradiating with an activating energy beam, it is preferably removed prior to irradiation with the activating energy beam in order to accurately control the dimensions and shape of the channel.

Examples of radiated activating energy beams include light rays such as ultraviolet rays, visible light rays, infrared rays, laser light rays and radiant light rays; ionizing radiation such as X-rays, gamma rays and radiant light rays; and particle beams such as electron beams, ion beams, beta rays and heavy particle beams. Among these, ultraviolet rays or visible light is preferable in terms of handling ease and curing rate, while ultraviolet rays are particularly preferable. Irradiation with an activating energy beam is preferably carried out in a low oxygen concentration atmosphere for the purpose of accelerating curing rate and ensuring complete curing. Preferable examples of low oxygen concentration atmospheres include a vacuum or reduced pressure atmosphere in the presence of flowing nitrogen, flowing carbon dioxide or flowing argon.

The aforementioned activating energy beam is radiated in a pattern when radiating the activating energy beam in order to form an indentation in which a porous resin layer having a three-dimensional mesh structure is formed on all or a portion of the bottom surface. The method employed for patterning radiation is arbitrary, and examples of methods that can be used include radiating the activating energy beam after masking the portion that is not to be irradiated with the activating energy beam, and photolithography involving scanning with a laser or other activating energy beam. In the case of using a photomask, the photomask may be of a non-contact type or contact type with the coating.

Adhesion with another member serving as a cover is possible without using an adhesive by curing or semi-curing an uncured coating of composition (X), or adhesive strength is improved in the case of using an adhesive. In the case composition (X) is in a semi-cured state, although it is preferable to completely cure composition (X) by carrying out post-curing in any step prior to obtaining the final microfluidic device, composition (X) is not required to be completely cured provided it does not impair the function of a microfluidic device of the present invention. In the case of curing using an activating energy beam, post-curing may use the same or different activating energy beam as that used for semi-curing. Post-curing may also be carried out by heat curing in addition to curing by an activating energy beam.

In step (3), another member serving as a cover is adhered to the indentation of a member having an indentation formed in step (2) to allow the aforementioned indentation to serve as a cavity-like channel.

The member that serves as a cover can be suitably selected according to the purpose of use, a member should be used that is not attacked by the liquid that flows through the channel, and said member may be in the form of a tape, sheet or plate having stickiness.

A cover member and a member having an indentation should be laminated in order to cover the indentation with the member serving as a cover. As previously described, the member having an indentation may be laminated as is if it is a semi-cured coating and has satisfactory adhesiveness with the cover member. In addition, in the case the adhesiveness of the member having an indentation is low or is a cured coated film, both members should be laminated using an adhesive and so forth.

In addition, a method may also be employed in which a composition containing an activating energy beam-polymerizeable compound is coated onto a substrate such as a polymer film or sheet, the substrate is irradiated with an activating energy beam to semi-cure the coating of said composition, and the substrate is laminated onto an indication of a member having the aforementioned indentation followed by again irradiating with an activating energy beam to completely cure the coated film of said composition. The activating energy beam-polymerizeable compound and its composition used here may be the same as polymerizeable compound (a) and composition (X) used in the aforementioned step (2), and may one or more types of compounds selected from the group of compounds listed as examples of compounds that can be used for polymerizeable compound (a). Coating of the polymerizeable compound should also be in compliance with step (2).

Examples of adhesives that can be used as adhesives when laminating the cover member and member having an indentation include epoxy resin-based adhesives, styrene butadiene resin-based adhesives and (meth)acrylic adhesives.

The use of a production process of the present invention makes it possible to easily obtain a microfluidic device having a porous resin layer having a three-dimensional mesh structure of uniform thickness on the inner surface of a minute channel without obstructing said channel. In addition, according to said production process, since a plurality of microfluidic devices can be easily fabricated on a single substrate (exposed developing plate) without requiring positioning, a large number of microfluidic devices can be produced all at once with satisfactory reproducibility and superior dimensional stability.

Among microfluidic devices obtained according to the aforementioned process, a microfluidic device that forms a cavity by (I) having a porous resin layer having a three-dimensional mesh structure on the upper portion of a substrate, (II) filling said porous resin layer with a cured resin of an activating energy beam-curable composition (X) impregnated except for a channel portion, and (III) having a porous resin layer having a three-dimensional mesh structure in which the channel is not filled with a cured resin of activating energy beam-curable composition (X), a cured resin layer of activating energy beam-curable composition (X) formed in the upper portion of a porous resin layer having a three-dimensional mesh structure filed with a cured resin of activating energy beam-curable composition (X), and a cover, serving as wall surfaces, can be used particularly preferable for a microfluidic device composed of a substrate, porous resin layer, channel and cover.

The size of the aforementioned channel cross-section should be a size that allows interaction between a separation target substance contained in the fluid flowing through the channel and the porous resin layer having a three-dimensional mesh structure, and in the case of a channel cross-section at a portion of the channel having the porous resin layer having a three-dimensional mesh structure, if an arbitrary point in said cross-section is designated as x, the portion of the porous resin layer having a three-dimensional mesh structure that is closest to said arbitrary point in terms of straight line distance is designated as y, the straight line distance between x and y is designated as r, and the maximum distance that r is able to have in said cross-section is designated as $r_{max}$, then the microfluidic device should be designed so that said $r_{max}$ is within the range of 1 to 50 μm. If the value of $r_{max}$ defined here is 50 μm or less, a separation target substance contained in the liquid that flows through the channel is able to satisfactorily interact with the porous resin layer having a three-dimensional mesh structure on the inner walls of the channel. In addition, if the value of $r_{max}$ is 1 μm or more, then the pressure required to cause the flow of the liquid does not become excessively large.

The microfluidic device should be suitably designed according to the arrangement of the porous resin layer having a three-dimensional mesh structure and the cross-sectional shape of the channel so that the value of $r_{max}$ in the channel cross-section is within the aforementioned range. For example, in the case of a channel having a porous resin layer having a three-dimensional mesh structure on the bottom and top of the inner walls and having a rectangular or trapezoidal cross-section, the height of the channel cross-section should be 100 μm or less, while in the case of a channel having a porous resin layer having a three-dimensional mesh structure only one surface of the inner walls and having a rectangular or trapezoidal cross-section, the distance between said porous resin layer and the side opposing said porous resin layer should be 1 to 50 μm. In the case of a channel having a circular or triangular cross-section, the microfluidic device should be similarly suitable designed according to the porous resin layer having a three-dimensional mesh structure of the inner walls. Furthermore, in the present invention, a rectangular or trapezoidal cross-section includes a shape having rounded corners.

On the other hand, the ratio between the maximum width and maximum height of the channel cross-section, as represented in the form of the ratio of maximum width to maximum height (maximum width/maximum height), is preferably within the range of 1/20 to 20/1, and particularly preferably within the range of 1/10 to 10/1, in terms of the ease of optically reading the spot of an analysis target substance flowing through the channel, the ease of controlling the flow rate, temperature and so forth, and the ease of production.

Channel length is arbitrary, and although a suitable length can be adopted according to the purpose of use, it is preferably 1 to 500 mm and more preferably 5 to 200 mm. If the channel length is greater than or equal to the aforementioned lower limit, adequate separation performance can be obtained, and if the channel length is less than or equal to the aforementioned upper limit, the required liquid pumping rate can be decreased, separation time can be shortened, and the size of the channel can be reduced.

In addition, the form of the direction parallel to the direction of liquid flow through the channel is arbitrary, and may be linear, curved or a combination thereof or branched. The width of the channel is also not required to be constant. In addition, the locations and quantity of channel openings are also arbitrary, and a single channel may have a plurality of openings. In addition, the number of independent channels present in a single member is also arbitrary.

A channel of a microfluidic device of the present invention has a porous resin layer having a three-dimensional mesh structure on one of its inner wall surfaces or on two opposing surfaces.

A non-porous member can be used as a cover for forming a porous resin layer having a three-dimensional mesh structure on one surface inside a channel. A member in which a porous resin layer having a three-dimensional mesh structure is formed on a substrate as previously described, or a member having a groove on said porous resin layer, for example, can be used as a cover to form a porous resin layer having a three-dimensional mesh structure on two opposing surfaces of channel inner walls.

The aforementioned porous resin layer having a three-dimensional mesh structure is formed on one surface or two opposing surfaces of the walls of a channel, and an analysis target substance that flows through the channel is separated as a result of moving through the channel while interacting with said porous resin layer. In addition, in the case of a probe being fixed to said porous resin layer, a target analysis substance is separated as a result of moving through the channel while interacting with said probe.

The formed site of a porous resin layer having a three-dimensional mesh structure in a direction parallel to the direction of movement of liquid through a channel may be the entire channel or partway through the channel. In the case the present microfluidic device is, for example, a chromatography device or electrophoresis analysis device, forming said porous resin layer continuously and without interruption in the channel is preferable for improving separation performance.

The thickness of the aforementioned porous resin layer having a three-dimensional mesh structure is preferably 0.5 to 30 μm, more preferably 1 to 20 μm, and most preferably 2 to 10 μm. By making the thickness equal to or greater than this lower limit, the surface area for interaction with an analysis target substance is sufficiently large, and separation performance is enhanced. On the other hand, making the thickness less or equal to the upper limit prevents a separation target substance in solution from penetrating inside deep pores causing a decrease in the migration rate, thereby making it possible to shorten separation and analysis times.

Although the pore diameter of the pores of the aforementioned porous resin layer having a three-dimensional mesh structure is arbitrary, it is preferably 0.05 to 3 μm, and more preferably 0.1 to 1 μm. By making the pore diameter equal to or greater than this lower limit, an adequate amount of probe can be fixed. In addition, by making the pore diameter less than or equal to the upper limit, since macromolecules like proteins can also be fixed as probes, the substance migration rate between the deep portion and surface of the porous resin layer having a three-dimensional mesh structure increases, thereby allowing rapid separation. Furthermore, the aforementioned pore diameter is the pore diameter of a large number of pores, and does not necessarily refer to the mean diameter. A narrow distribution of the aforementioned pore diameter is preferable since it results in higher separation efficiency.

Although the porosity of the aforementioned porous resin layer having a three-dimensional mesh structure is arbitrary, it is preferably 30 to 90%, and more preferably 40 to 70%. If porosity is made to be within this range, surface area can be adequately increased without causing a decrease in mechanical strength.

The previously described organic polymers can be used for the material of the aforementioned porous resin layer having a three-dimensional mesh structure, and the material is more preferably an activating energy beam-curable resin since it can be molded easily. In the case of fixing a probe, although a material that facilitates probe fixation can be arbitrarily selected, it is preferably an organic polymer since production is easy, and it is more preferably an activating energy beam-curable resin since it can be molded easily.

In addition, arbitrary functional groups can be introduced into the aforementioned porous resin layer having a three-dimensional mesh structure. Examples of hydrophilic functional groups include nonionic functional groups such as hydroxyl groups, polyethylene glycol groups, amide groups and nitro groups, anionic functional groups such as carboxyl groups, sulfone groups, phosphoric acid groups, phosphorous acid groups, (substituted) hydroxyphenyl groups and silanol groups, and cationic functional groups such as (N-substituted) amino groups, quaternary ammonium groups, phosphonium groups and sulfonium groups. Examples of hydrophobic functional groups include fluorine, chlorine groups, siloxane structures, alkyl groups and phenyl groups. Examples of amphoteric functional groups include amino acid residues. Other examples of functional groups include amphiphilic functional groups. Other examples also include photoreactive groups such as azides. Furthermore, these functional groups may be made to function themselves such as by imparting selective adsorptivity, they can be converted into active functional groups by a chemical reaction, or they can be used as anchors for fixing (bio)chemical substances or biological substances and so forth.

Other substances are also preferably fixed to the aforementioned porous resin layer having a three-dimensional mesh structure. Examples of other substances include various types of catalysts, enzymes, antibodies, antigens and other proteins, oligonucleotides such as DNA and RNA, sugar-containing substances such as sugar chains and glycolipids, biological tissue such as cell membranes, organelle and cells, and living organisms such as bacteria. These substances may naturally also be chemically modified. In the case of using an oligonucleotide as a fixed probe in particular, genes can be separated and detected, thereby allowing these substances to be used effectively for the detection of single-base gene mutations.

In the case of using an oligonucleotide as a probe, the length of the oligonucleotide is preferably 5 to 30 nucleotides, more preferably 5 to 20 nucleotides, and most preferably 5 to 10 nucleotides. By making the length of the oligonucleotide within this range, a sufficiently reliable and high separation rate can be obtained at a temperature that allows the present invention to be carried out easily, namely from room temperature to 60° C. In addition, it is also preferable for the same purpose to use an oligonucleotide comprised of a nucleotide sequence that intentionally contains mismatches with respect to a polynucleotide or oligonucleotide targeted for analysis for the probe oligonucleotide.

In the case of using a microfluidic device of the present invention as a liquid chromatography column, the amount of probe (including functional groups) fixed to the surface of the channel is preferably in excess with respect to the amount of analysis target substance having affinity with the probe. In the case the amount of probe is in excess, the amount of analysis target substance involved in interaction with the probe increases as compared with only using an insufficient amount of probe, and since the local concentration of target analysis substance becomes higher, the target analysis substance can be detected with high sensitivity. For reasons such as this, the greater the amount of probe fixed to the porous resin layer having a three-dimensional mesh structure, the better.

In addition, in the case of using a microfluidic device of the present invention as a member for affinity electrophoresis as well, the amount of probe fixed is preferably large as in the aforementioned case of liquid chromatography.

EXAMPLES

Although the following provides a more detailed explanation of the present invention using its examples, the present invention is not limited to the scope of these examples. Furthermore, in the following examples, the terms "parts" and "%" respectively refer to "parts by weight" and "% by weight" unless indicated otherwise.

Measurement of viscosity and irradiation with an ultraviolet lamp in the examples were carried out using the methods indicated below.

[Viscosity Measurement]

The viscosity of a composition at 25° was measured using the Model VDH-K viscometer manufactured by Shibaura Systems Co., Ltd.

[Irradiation with Ultraviolet Lamp 1]

Ultraviolet light having an ultraviolet intensity of 40 mW/cm$^2$ at 365 nm was radiated at room temperature in a nitrogen atmosphere unless indicated otherwise using the Model UE031-353CHC UV Radiation Device manufactured by Eyegraphics Co., Ltd., which uses a 3000 W metal halide lamp for the light source.

[Irradiation with Ultraviolet Lamp 2]

Ultraviolet light having an ultraviolet intensity of 100 mW/cm$^2$ at 365 nm was radiated at room temperature in a nitrogen atmosphere unless indicated otherwise using the light source unit of the Multilight Model 200 UV Exposure Device manufactured by Ushio Inc. which uses a 200 W metal halide lamp for the light source.

Example 1

The present example 1 is an example of producing a porous resin layer having a three-dimensional mesh structure according to the "reaction induction-type phase separation method".

[Preparation of Membrane Deposition Liquid (J)]

72 parts of a trifunctional urethane acrylate oligomer (Unidic V-4263, Dainippon Ink and Chemicals) having an average molecular weight of 2000, 18 parts of dicyclopentanyl diacrylate (R-684, Nippon Kayaku), 10 parts of glycidyl methacrylate (Wako Pure Chemical Industries), 150 parts of methyl decanoate (Wako Pure Chemical Industries), 10 parts of a volatile good solvent in the form of acetone, and 3 parts of an ultraviolet polymerization initiator in the form of 1-hydroxycyclohexyl phenyl ketone (Irgacure 184, Ciba-Geigy) were uniformly mixed to prepare membrane deposition liquid (J1).

[Preparation of Composition (X)]

50 parts of a trifunctional urethane acrylate oligomer (Unidic V-4263, Dainippon Ink and Chemicals) having an average molecular weight of 2000, 40 parts of hexanediol diacrylate (New Frontier HDDA, Daiichi Pharmaceutical), 10 parts of glycidyl methacrylate (Wako Pure Chemical Industries), 5 parts of a photopolymerization initiator in the form of 1-hydroxycyclohexyl phenyl ketone (Irgacure 184, Ciba-Geigy) and 0.5 parts of polymerization retardant in the form of 2,4-diphenyl-4-methyl-1-pentene (Kanto Chemical) were mixed to prepare composition (X1). The viscosity of said composition (X1) was 192 mPa·s.

[Step 1: Formation of Porous Resin Layer Having a Three-Dimensional Mesh Structure]

Membrane deposition liquid (J1) was coated at a rotating speed of 600 rpm using a spin coater (Mikasa) onto an acrylic sheet having a thickness of 1 mm used as a substrate, and said deposition liquid (J1) was irradiated for 40 seconds with ultraviolet light from ultraviolet lamp 1 to cure membrane deposition liquid (J1) followed by washing with n-hexane to remove poor solvent (R) to form a porous resin layer (1) having a three-dimensional mesh structure.

[Step 2: Formation of Indentation (Channel) in Which Porous Resin Layer Having a Three-Dimensional Mesh Structure is Exposed on Bottom Surface]

Composition (X1) was coated at a rotating speed of 800 rpm using a spin coater (Mikasa) onto the aforementioned porous resin layer (1) having a three-dimensional mesh structure to form an uncured coating of said composition (X1), said uncured coating was irradiated for 120 seconds with ultraviolet light from ultraviolet lamp 2 through a photomask at locations other than where the channel is to be formed to form a semi-cured coating of said composition (X1), and the non-irradiated portion of uncured composition (X1) was removed with ethanol to form an indentation (channel 1) on the substrate in which porous resin layer (1) having a three-dimensional mesh structure is exposed on the bottom surface.

[DNA Fixation]

(Introduction of Amino Groups)

A 5% by weight aqueous solution of polyallylamine (molecular weight: 15000, Nitto Boseki) was contacted with the indentation (channel 1) prepared in the aforementioned step 2 and allowed to react for 2 hours at 50° C. (a portion of the amino groups in the polyallylamine were reacted with epoxy groups in the porous resin layer having a three-dimensional mesh structure), followed by washing for 15 minutes under running water to introduce amino groups into said porous resin layer.

(Introduction of Aldehyde Groups)

A substrate having the aforementioned indentation (channel 1) into which amino groups were introduced was placed in a 5% by weight aqueous solution of glutaraldehyde (Wako Pure Chemical Industries) and allowed to react for 2 hours at 50° C. (nearly all of the amino groups in the polyallylamine were reacted with one of the aldehyde groups of glutaraldehyde), followed by washing for 10 minutes under running water to introduce aldehyde groups into the porous resin layer having a three-dimensional mesh structure.

(DNA Fixation)

One μL of an aqueous solution (concentration: 50 μM) of DNA having an amino-modified 5' terminal and a fluorescein isothiocyanate isomer I (FICT-I)-modified 3' terminal (length: 25 nucleotides, Espec Oligo Service) was dropped into the aforementioned indentation (channel 1) in which aldehyde groups were introduced, and after reacting for 15 minutes at 50° C. and humidity of 100% (the terminal amino groups of DNA were allowed to react with the aldehyde groups of the porous resin layer having a three-dimensional mesh structure), the indentation was placed in a 0.2% by weight aqueous solution of sodium tetrahydroborate and allowed to undergo a reduction reaction for 5 minutes. Next, the indentation was rinsed with 0.2×SSC/0.1% SDS solution and then rinsed with 0.2×SSC followed by additionally rinsing with distilled water and allowing to air dry to fix the DNA to the porous resin layer having a three-dimensional mesh structure on the bottom surface of the indentation (channel 1). (Here, 0.2×SSC refers to an aqueous solution of 0.03 M NaCl and 3 mM sodium citrate, while 0.1% SDS refers to an aqueous solution of 0.1% by weight sodium dodecyl sulfate.)

[Step 3: Adhesion of Cover]

A composition in which 72 parts of a trifunctional urethane acrylate oligomer (Unidic V-4263, Dainippon Ink and Chemicals) having an average molecular weight of 2000, 18 parts of hexanediol diacrylate (New Frontier HDDA, Daiichi Pharmaceutical), 10 parts of glycidyl methacrylate (Wako Pure Chemical Industries) and 2 parts of a photopolymerization initiator in the form of 1-hydroxycyclohexyl phenyl ketone (Irgacure 184, Ciba-Geigy) were uniformly mixed, was coated at a rotating speed of 800 rpm using a spin coater (Mikasa) onto a biaxially oriented polypropylene film having a thickness of 30 μm subjected to corona discharge treatment on one side (Futamura Chemical). Said uncured coating was irradiated for 1 second with ultraviolet light from ultraviolet lamp 1 to form a semi-cured film of the aforementioned composition. This was laminated over the indentation (channel 1) fabricated in the aforementioned step 2 and completely cured by again irradiating with ultraviolet light from ultraviolet lamp 1 for 40 seconds to produce a microfluidic device (1) having a capillary-like channel (channel 1) in which a porous resin layer having a three-dimensional mesh structure is exposed on the bottom surface.

[Observation of Structure of Porous Resin Layer Having a Three-Dimensional Mesh Structure]

Figure 1:
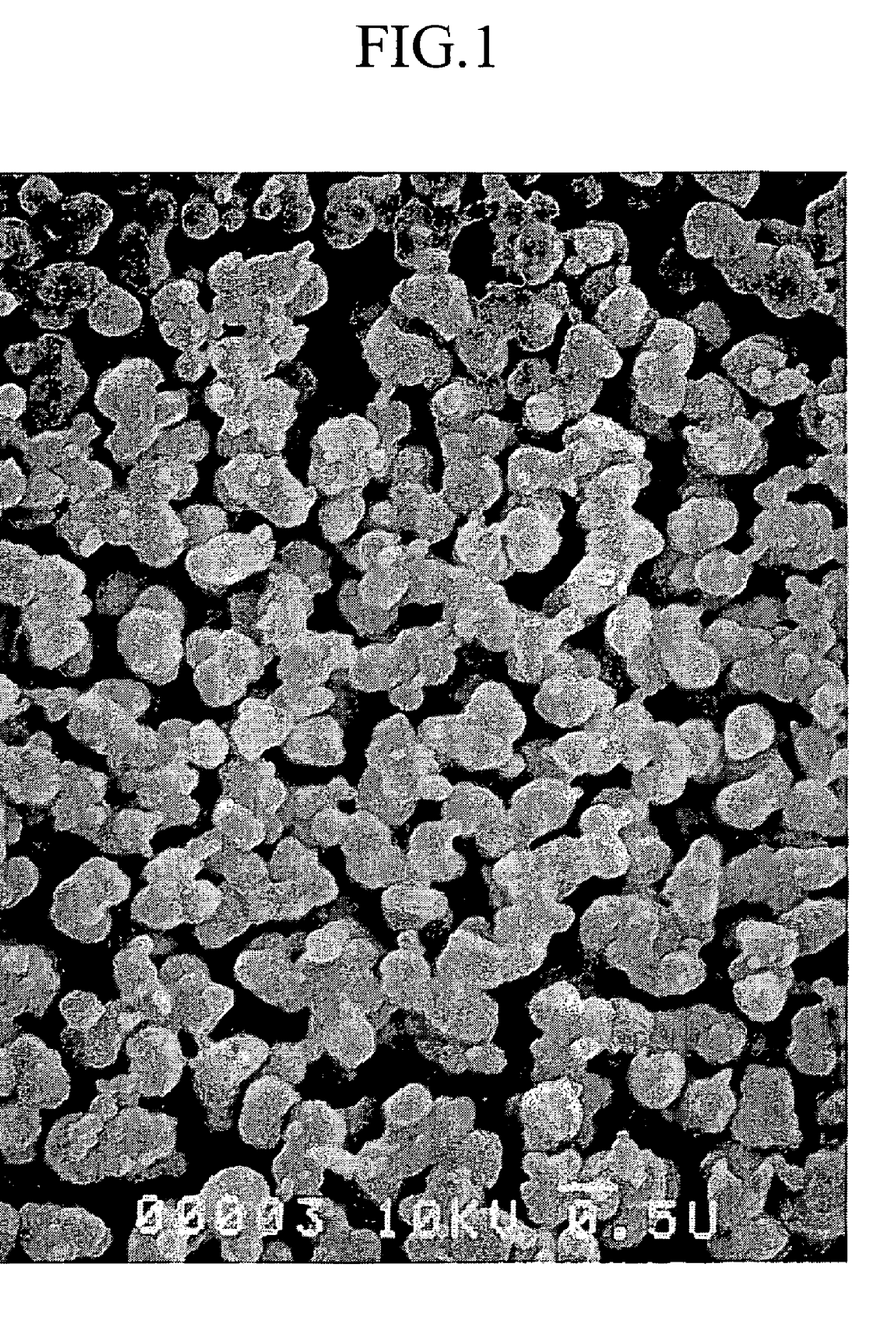
FIG. 1 is a scanning electron micrograph of a porous resin layer having a three-dimensional mesh structure produced in Example 1.

When the surface of the aforementioned porous resin layer having a three-dimensional mesh structure fabricated in step 1 was observed with a scanning electron microscope, pores having a pore diameter of about 0.4 μm were observed in the form of cavities between aggregated particles having a diameter of about 0.5 μm. In addition, when a cross-section of the porous resin layer having a three-dimensional mesh structure was observed, the thickness of said porous resin layer having a three-dimensional mesh structure was about 10 μm. A scanning electron micrograph of said porous resin layer having a three-dimensional mesh structure is shown in FIG. 1.

[Observation of Structure of Indentation (Channel)]

When a cross-section of the indentation (channel 1) fabricated in the aforementioned step 2 was observed with a scanning electron microscope, the cross-sectional shape of the indentation was rectangular having a width of about 250 μm and a depth, excluding the porous resin layer having a three-dimensional mesh structure, of about 30 μm.

[DNA Quantification]

As a result of measuring the fluorescent intensity emitted by the FITC-I in the porous resin layer, having a three-dimensional mesh structure on the bottom surface to which the aforementioned DNA was fixed, with a Fluoro Imaging Scanner (FLA-3000G, Fuji Photo Film), the value of fluorescent intensity was 1069 LAU (units of fluorescent intensity displayed on the aforementioned instrument)/mm$^2$.

Example 2

The present Example 2 is an example of producing a porous resin layer having a three-dimensional mesh structure according to the "surface swelling method".

[Preparation of Composition (X)]

A composition (X2) was prepared in the same manner as the preparation of composition (X1) in Example 1 with the exception of mixing 40 parts of 1,6-hexanediol ethoxylate diacrylate (Photomer 4361, Cognis Japan) instead of 40 parts of hexanediol diacrylate (New Frontier HDDA, Daiichi Pharmaceutical), and mixing 10 parts of nonylphenoxy polyethylene glycol (n=17) acrylate (N-177E, Daiichi Pharmaceutical) instead of 10 parts of glycidyl methacrylate (Wako Pure Chemical Industries). The viscosity of this composition was 220 mPa·s.

[Step 1: Formation of Porous Resin Layer Having a Three-Dimensional Mesh Structure]

(Formation of Three-Dimensional Mesh Structure)

After immersing a polystyrene sheet (Dainippon Ink and Chemicals) having a thickness of 150 μm used as a substrate in N,N-dimethylacetoamide (Wako Pure Chemical Industries) for 5 seconds at room temperature, the sheet was placed in water and additionally washed for about 5 minutes under running water to obtain a polystyrene sheet in which a porous resin layer having a three-dimensional mesh structure and substrate were integrated into a single unit.

(Introduction of Epoxy Groups)

Moreover, a composition in which was mixed 2.5 parts of a trifunctional urethane acrylate oligomer (Unidic V-4263, Dainippon Ink and Chemicals) having an average molecular weight of 2000, 2 parts of 1,6-hexanediol ethoxylate diacrylate (Photomer 4361, Cognis Japan), 0.5 parts of glycidyl methacrylate (Wako Pure Chemical Industries), 0.25 parts of a photopolymerization initiator in the form of 1-hydroxycyclohexyl phenyl ketone (Irgacure 184, Ciba-Geigy) and 95 parts of a solvent in the form of ethanol, was coated at a rotating speed of 1500 rpm using a spin coater (Mikasa) onto said porous resin layer having a three-dimensional mesh structure, followed by irradiating for 40 seconds with ultraviolet light from ultraviolet lamp 1 to form a porous resin layer (2) having a three-dimensional mesh structure in which epoxy groups are introduced onto the pore surfaces.

[Step 2: Formation of Indentation (Channel) in Which Porous Resin Layer is Exposed on Bottom Surface]

An indentation (channel 2) in which a porous resin layer having a three-dimensional mesh structure is exposed on the bottom surface was formed using the same method as Example 1 with the exception of using composition (X2) instead of composition (X1).

[DNA Fixation]

Introduction of amino groups and aldehyde groups, and fixation of DNA were carried out in the same manner as Example 1.

[Step 3: Adhesion of Cover]

A cover was adhered to the indentation (channel 2) using the same composition and same method as in the case of Example 1 to produce a microfluidic device (2) having a capillary-like channel (channel 2) in which a porous resin layer having a three-dimensional mesh structure is exposed on the bottom surface.

[Observation of Structure of Porous Resin Layer Having a Three-Dimensional Mesh Structure]

When the surface of the aforementioned porous resin layer (2) having a three-dimensional mesh structure fabricated in step 1 was observed with a scanning electron microscope, sponge-like pores having a pore diameter of about 0.8 μm were observed. In addition, when a cross-section of said porous resin layer was observed, the thickness of said porous resin layer was about 2 μm.

[Observation of Structure of Indentation (Channel)]

When a cross-section of the indentation (channel 2) fabricated in the aforementioned step 2 was observed with a scanning electron microscope, the cross-sectional shape of the indentation was rectangular having a width of about 250 μm and a depth, excluding the porous resin layer having a three-dimensional mesh structure, of about 30 μm.

[DNA Quantification]

DNA was fixed to the indentation (channel 2) formed in the aforementioned step 2 using the same method as the DNA fixation method indicated in the aforementioned Example 1. As a result of measuring the fluorescent intensity emitted by FITC-I fixed to said indentation (channel 2) using the same method as the DNA quantification of Example 1, the value of fluorescent intensity was 954 LAU/mm$^2$.

Example 3

The present example 3 is an example of producing a porous resin layer having a three-dimensional mesh structure according to the "wet method".

[Preparation of Membrane Deposition Liquid (K)]

5 parts of a linear polymer in the form of an aromatic polyamide (Conex, Teijin), 90 parts of a solvent (U) in the form of N,N-dimethylacetoamide (Wako Pure Chemical Industries), and 5 parts of an additive in the form of ethylene glycol were uniformly mixed to obtain membrane deposition liquid (K).

[Preparation of Composition (X)]

50 parts of tritetraethylene glycol bis-maleimide (Lumicure MIA200, Dainippon Ink and Chemicals), 40 parts of 1,6-hexanediol ethoxylate diacrylate (Photomer 4361, Cognis Japan), 10 parts of N,N-dimethylacrylamide (DMAA, Kohjin), and 0.5 parts of polymerization retardant in the form of 2,4-diphenyl-4-methyl-1-pentene (Kanto Chemical) were mixed to prepare composition (X3). The viscosity of said composition (X3) was 100 mPa·s.

[Step 1: Formation of Porous Resin Layer Having a Three-Dimensional Mesh Structure]

(Formation of Three-Dimensional Mesh Structure)

Membrane deposition liquid (K) was coated using a 50 μm bar coater onto an acrylic sheet having a thickness of 1 mm used as a substrate, and said substrate was immersed in water to obtain a milky white, coagulated coating. The resulting coagulated coating was additionally washed for 10 minutes under running water and then dried for 1 hour in a vacuum at 40° C. to obtain a porous resin layer having a three-dimensional mesh structure.

[Step 2: Formation of Indentation (Channel) in Which Porous Resin Layer Having a Three-Dimensional Mesh Structure is Exposed on Bottom Surface]

An indentation (channel 3) in which porous resin layer (3) having a three-dimensional mesh structure is exposed on the bottom surface was formed using the same method as Example 1 with the exception of using composition (X3) instead of composition (X1).

(DNA Fixation)

The introduction of amino and aldehyde groups as well as DNA fixation were carried out in the same manner as Example 1.

[Step 3: Adhesion of Cover]

A cover was adhered to the indentation (channel 3) using the same composition and same method as in the case of Example 1 to produce a microfluidic device (3) having a capillary-like channel (channel 3) in which a porous resin layer having a three-dimensional mesh structure is exposed on the bottom surface.

[Observation of Structure of Porous Resin Layer Having a Three-Dimensional Mesh Structure]

When the surface of the aforementioned porous resin layer (3) having a three-dimensional mesh structure fabricated in step 1 was observed with a scanning electron microscope, sponge-like pores having a pore diameter of about 0.6 μm were observed. In addition, when a cross-section of said porous resin layer was observed, the thickness of said porous resin layer was about 35 μm.

[Observation of Structure of Indentation (Channel)]

When a cross-section of the indentation (channel 3) fabricated in the aforementioned step 2 was observed with a scanning electron microscope, the cross-sectional shape of the indentation was rectangular having a width of about 250 μm and a depth, excluding the porous resin layer having a three-dimensional mesh structure, of about 30 μm.

Comparative Example 1

The present comparative example relates to a microfluidic device which uses the surface of a known amino group-fixing glass substrate for the bottom surface of a channel, and indicates that the DNA fixation density is low.

[Formation of Indentation (Channel)]

Composition (X1) produced in Example 1 was coated at a rotating speed of 800 rpm using a spin coater (Mikasa) onto a slide glass in which amino groups were introduced onto the surface (Amine Silane, Matsunami Glass Industries) to form an uncured coating of said composition (X1), said uncured coating was irradiated for 120 seconds with ultraviolet light from ultraviolet lamp 2 through a photomask at locations other than where the channel is to be formed to form a semi-cured coating of said composition (X1), and the non-irradiated portion of uncured composition (X1) was removed with ethanol to form an indentation (channel 4) where the glass was exposed on the bottom surface.

[DNA Fixation]

The aforementioned indentation (channel 4) having amino groups on its bottom surface was subjected to glutaraldehyde treatment using the same method as Example 1 to introduce aldehyde groups onto the bottom surface.

Next, the aforementioned indentation (channel 4) in which aldehyde groups were introduced was treated in the same manner as Example 1 to carry out DNA fixation.

[DNA Quantification]

As a result of measuring the aforementioned indentation (channel 4) in which DNA was fixed to glass on the bottom surface in the same manner as Example 1, the value of fluorescent intensity was 73 LAU/mm$^2$.

Comparative Example 2

The present comparative example indicates that the amount of DNA fixed to a silicon substrate surface is low. However, measurements were performed without forming an indentation.

[Introduction of Amino Groups]

After pre-treating a silicon wafer by irradiating with ultraviolet light in a vacuum (Sen Koki), the wafer was immersed in a 1 mM isopropanol solution containing a silane coupling agent having amino groups in the form of 3-aminopropyl triethoxysilane (LS-3150, Shin-Etsu Silicones) for 3 hours at 25° C. followed by washing with ethanol and hot air drying for 30 minutes at 80° C. to introduce amino groups onto the surface of the silicon wafer.

[DNA Fixation]

Glutaraldehyde treatment and amino group modification DNA treatment were carried out in the same manner as Example 1 on the surface of the aforementioned silicon wafer on which amino groups had been introduced to fix DNA to the surface of the silicon wafer.

[DNA Quantification]

As a result of measuring the surface of the aforementioned silicon wafer on which DNA had been fixed using the same method as Example 1, the value of fluorescent intensity was about 78 LAU/mm$^2$.

Comparative Example 3

The present comparative example indicates that the amount of DNA fixed to a silicon porous layer is low. However, measurements were performed without forming a channel.

[Formation of Porous Channel]

A porous layer having a width of 250 μm and a depth from the surface of a silicon wafer of about 30 μm was formed in accordance with the process described in Japanese Unexamined Patent Application, First Publication No. H6-169756 using a silicon wafer.

[Introduction of Amino Groups]

Amino groups were introduced into this porous layer in the same manner as Comparative Example 2.

[DNA Fixation]

DNA was fixed to this porous layer in the same manner as Comparative Example 2.

[DNA Quantification]

As a result of measuring the surface of the aforementioned porous layer on which DNA had been fixed to bottom surface porous silicon using the same method as Example 1, the value of fluorescent intensity was about 114 LAU/mm$^2$. Namely, fluorescent intensity only increased about 1.46 times as compared with a smooth silicon wafer surface.

Comparative Example 4

The present comparative example indicates that the amount of DNA fixed to surface having surface irregularities formed by electron beam etching is low.

[Formation of Surface Irregularities]

An acrylic sheet was etched with an electron beam for 5 minutes at 15 mA using the Model E1030 Ion Sputtering System (Hitachi) to provide surface irregularities having a depth of about 0.4 μm in the surface.

[Production of Microfluidic Device]

A microfluidic device was produced by carrying out epoxy group introduction, channel formation, amino group introduction, aldehyde group introduction, DNA fixation and cover adhesion in the same manner as Example 2 with the exception of using an acrylic sheet in which surface irregularities were formed in the manner described above instead of an acrylic sheet on which was formed a porous resin layer having a three-dimensional mesh structure.

[DNA Quantification]

As a result of measuring in the same manner as Example 2, the value the value of fluorescent intensity was about 288 LAU/mm$^2$.

According to the DNA quantification results of the aforementioned Examples 1 to 3 and Comparative Examples 1 to 4, in comparison with the channel not having a porous resin layer of Comparative Example 1, a channel having a porous bottom surface made of silicon, or a channel having a simple irregular surface instead of a porous channel having a three-dimensional mesh structure, the specific surface area of the channels provided with a porous resin layer having a three-dimensional mesh structure of the examples was extremely large, and were clearly able to fix numerous substances.

INDUSTRIAL APPLICABILITY

Since a microfluidic device of the present invention has a thin porous resin layer adhered to the inner surface of a channel, the fixation of large amounts of functional groups, (bio)chemical substances or biological substances can be realized even in a minute region without obstructing the channel. In addition, since said porous resin layer has a three-dimensional mesh structure, said porous resin layer has an extremely large surface area, enabling it to fix a large amount of a probe. Moreover, a microfluidic device provided with a porous resin layer having a three-dimensional mesh structure on one or two inner surfaces of the aforementioned rectangular or trapezoidal channel, and particularly a microfluidic device in which the average distance from said porous resin layer to an opposing inner wall is within the range of 1 to 50 μm, is able to generate effective affinity between an analysis target substance that moves over said porous section and a fixed probe. Consequently, when a microfluidic device of the present invention is used, treatment such as synthesis, separation or analysis can be carried out accurately and quickly. In particular, a microfluidic device of the present invention can be preferably used for DNA analysis by using an oligonucleotide for the fixed probe.

The invention claimed is:

1. A microfluidic device comprising a substrate, a porous resin layer having a three-dimensional mesh structure, a channel and a cover; wherein, said microfluidic device (I) has said porous resin layer in the upper portion of the substrate, (II) said porous resin layer is filled with a curable resin of an activating energy beam-curable resin composition (X) impregnated excluding the channel portion, and (III) the channel has wall surfaces consisting of a porous resin layer having a three-dimensional mesh structure that is not filled with activating energy beam-curable resin composition (X), a curable resin layer of the activating energy beam-curable resin composition (X) formed in the upper portion of the porous resin layer having a three-dimensional mesh structure filled with the curable resin of activating energy beam-curable resin composition (X), and a cover, and is formed into the form of a cavity.

2. The microfluidic device according to claim 1, wherein the porous resin layer having a three-dimensional mesh structure is composed of an activating energy beam-curable resin composition.

3. The microfluidic device according to claim 1, wherein, in a cross-section in the direction perpendicular to the direction of flow of a fluid in a portion of the channel having a porous resin layer having a three-dimensional mesh structure, if an arbitrary point in said cross-section is designated as x, the portion of the porous resin layer having a three-dimensional mesh structure that is closest to said arbitrary point in terms of straight line distance is designated as y, the straight line distance between x and y is designated as r, and the maximum distance that r is able to have in said cross-section is designated as $r^{max}$, then said $r^{max}$ is within the range of 1 to 50 μm.

4. The microfluidic device according to claim 1, wherein the shape of a cross-section of the channel in the direction perpendicular to the direction of fluid flow is rectangular or trapezoidal.

5. The microfluidic device according to claim 4, wherein the porous resin layer having a three-dimensional mesh structure is formed on only one inner wall of the channel, and the average distance from said porous resin layer to the opposing inner wall is within the range of 1 to 50 μm.

6. The microfluidic device according to claim 1, wherein the thickness of the porous resin layer having a three-dimensional mesh structure is within the range of 0.5 to 30 μm.

7. The microfluidic device according to claim 1, wherein the mean pore diameter of the porous resin layer having a three-dimensional mesh structure is within the range of 0.05 to 3 μm.

8. The microfluidic device according to claim 1, wherein the porous resin layer having a three-dimensional mesh structure is a porous resin layer to which a probe having affinity for an analysis target substance is fixed.

9. The microfluidic device according to claim 8, wherein the probe is an oligonucleotide.

* * * * *